United States Patent [19]

Vadher

[11] Patent Number: 4,988,339

[45] Date of Patent: Jan. 29, 1991

[54] RETRACTABLE NEEDLE/SYRINGE DEVICES FOR BLOOD COLLECTION, CATHETERIZATION, AND MEDICINAL INJECTION PROCEDURES

[76] Inventor: Dinesh L. Vadher, 278 E. Main St., Smithtown, N.Y. 11787

[21] Appl. No.: 292,493

[22] Filed: Dec. 30, 1988

[51] Int. Cl.[5] ............................................. A61M 5/32
[52] U.S. Cl. .................................... 604/197; 604/117
[58] Field of Search ............... 604/117, 136, 187, 192, 604/197, 194, 198, 201, 218

[56] References Cited

U.S. PATENT DOCUMENTS

| | | | |
|---|---|---|---|
| 1,093,471 | 4/1914 | Porter | 604/191 |
| 3,046,985 | 7/1962 | Saenz | 604/197 |
| 3,306,290 | 2/1967 | Weltman . | |
| 3,368,558 | 2/1968 | Sarnoff . | |
| 4,194,505 | 3/1980 | Schmitz . | |
| 4,258,713 | 3/1981 | Wardlaw | 604/198 |
| 4,507,117 | 3/1985 | Vining | 604/196 |
| 4,553,962 | 11/1985 | Brunet | 604/198 |
| 4,664,654 | 5/1987 | Strauss | 604/198 |
| 4,747,829 | 5/1988 | Jacob | 604/198 |
| 4,747,831 | 5/1988 | Kulli | 604/198 |
| 4,767,413 | 8/1988 | Haber | 604/198 |
| 4,772,272 | 9/1988 | McFarland | 604/198 |
| 4,787,891 | 11/1988 | Levin et al. | 604/136 |
| 4,898,590 | 2/1990 | Andors . | |

OTHER PUBLICATIONS

Brochure entitled "Total Automatic Syringe Injection" from Ulster Scientific (4 sides).

Primary Examiner—C. Fred Rosenbaum
Assistant Examiner—Sharon Rose
Attorney, Agent, or Firm—Morgan & Finnegan

[57] ABSTRACT

Retractable needle/syringe devices for blood collection, catheterization, and medicinal injection procedures adapted to fixedly project the needle from a device housing to perform the procedure, and, after the procedure is completed, retract the needle back into the housing for disposal, substantially without risk of persons handling these devices coming into contaminating contact with a used needle or syringe. One embodiment of the device including a needle/syringe assembly spring biased in a first position within a housing. A push button locking mechanism disposed through the top of the housing in abutting alignment with the syringe barrel is operated to forwardly translate the syringe to a second position and lock it in place so as to fixedly project the needle from the housing. A plunger arm perpendicularly connected to the syringe plunger and projecting out of the housing through cooperating apertures formed on the syringe barrel and housing is operated to draw fluid (blood or medicament) into and discharge fluid from the syringe barrel. Thereafter, the push button is operated again to release the locking mechanism and retract the needle back into the housing. For use in medicinal injection procedures, an ampule filled with an injectant and formed with a front seal and a movable rear seal is frictionally enclosed by the barrel. A plunger mechanism connected to the rear seal of the ampule is operated to translate the ampule forward until the portion of the needle disposed within the barrel penetrates the front seal of the ampule and establishes fluid communication with the injectant. The front of the barrel provides a stop against further forward movement of the ampule pursuant to which further pressure applied to the knob will cause the rear seal to move forward so as to discharge the injectant from the ampule.

21 Claims, 4 Drawing Sheets

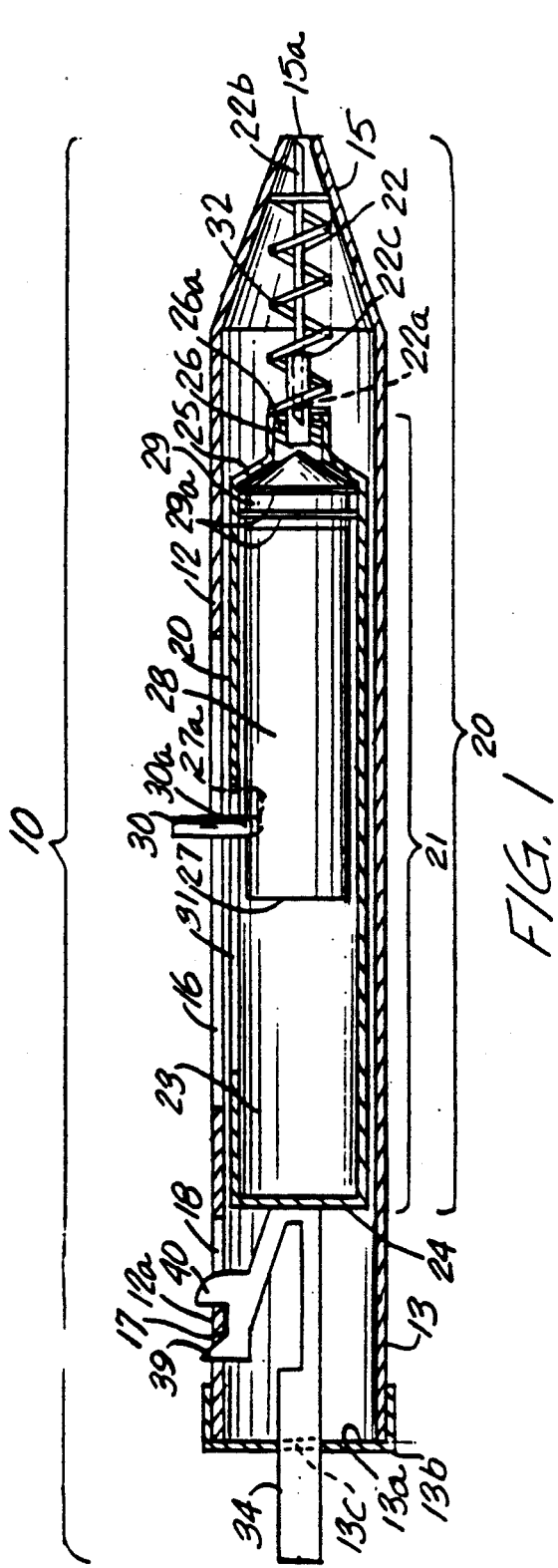
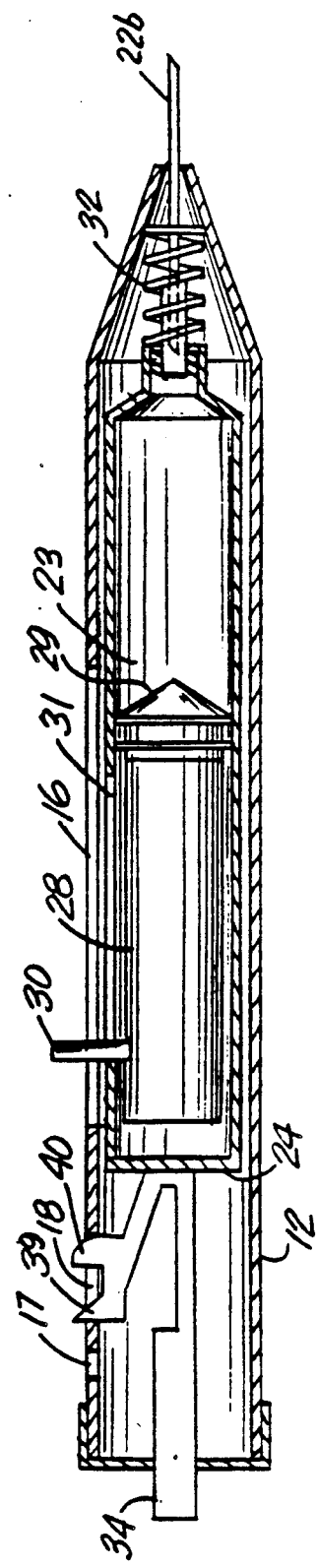

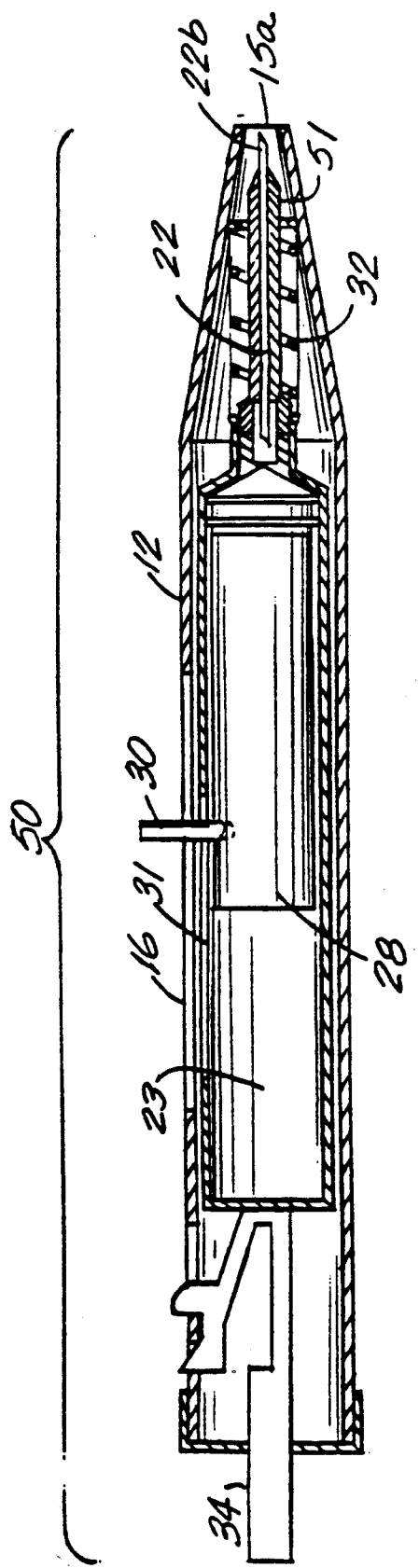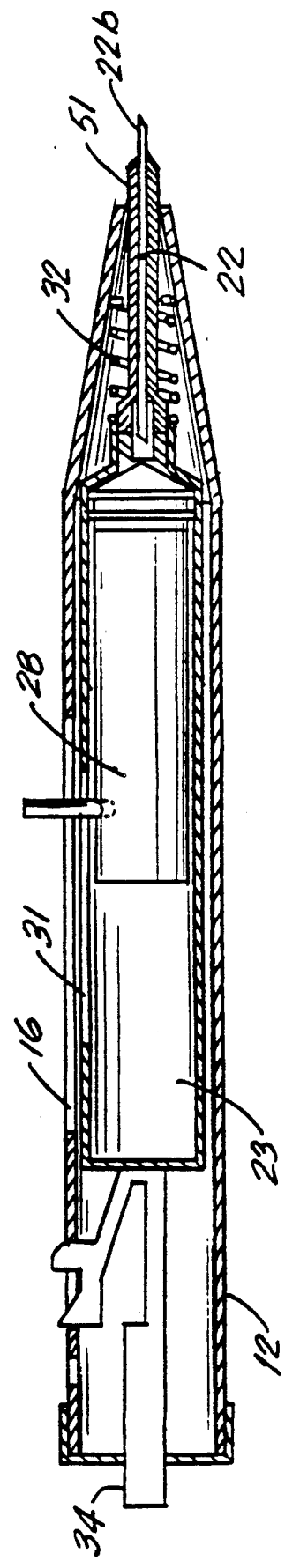

RETRACTABLE NEEDLE/SYRINGE DEVICES FOR BLOOD COLLECTION, CATHETERIZATION, AND MEDICINAL INJECTION PROCEDURES

BACKGROUND AND OBJECTS OF THE INVENTION

The present invention relates generally to devices which reduce the risk of infection associated with the use of disposable medical implements in hospitals and other medical facilities (such as a clinic or doctor's office), and, more particularly, to hypodermic needle/syringe devices used in blood collection and medicinal injection procedures, wherein the needle and syringe are pre-assembled in a device housing adapted to fixedly project the needle therefrom to perform the procedure, and, after the procedure is performed, safely retract the needle back into the housing for disposal, substantially without risk of contaminating contact by the operator of the device with the used needle or syringe.

In today's hospitals, a wide variety of disposable needle and syringe devices are routinely used to administer medication by injection, for intravenous blood collection, and for insertion of catheter devices. For the typical injection procedure, the nurse or medical technician will assemble a sterile needle/syringe device and pre-fill the syringe with medication at the nurses' station or at a medication cart outside the patient's room. During blood collection procedures, the nurse will assemble a sterile needle/syringe device to draw blood for immediate transfer to a vacuum tube collection device, or draw the blood directly into the collector by means of a multi-sample needle/collection tube holder device.

For catheter insertion procedures, the catheter tube is slipped over a hypodermic needle which is then grasped by its hub portion to guide the catheter into the patient's vein. Often, while the needle and catheter are held in place, a syringe is affixed to the needle hub and then operated to draw a small potion of blood from the vein to ensure that the catheter has been properly placed. Thereafter, the catheter is held in place and the needle is removed from the vein. The catheter will then be typically hooked up via a tubing connection to an intravenous ("I.V.") apparatus. A potential danger inherent in such a procedure results from the fact that once the needle guiding the catheter punctures the patient's vein, blood will shoot out through the needle and possibly onto the clothes or skin of the person performing the catheterization.

With the widespread use of disposable hypodermic needles and syringes, there exists a definite need for ways to safely and conveniently dispose of such implements after use without risk of exposing medical personal handling them to injury, infection or disease by puncture or contact with a used needle or syringe. Today's health professionals, especially those who attend to patients suffering from highly contagious diseases such as Acquired Immune Deficiency Syndrome ("AIDS") and Hepatitis, are acutely aware of such risks.

Once a needle and/or syringe is used, both implements are contaminated and must be disposed of in a safe manner. It had been once common practice to break or cut the needle after use before transport to ultimate disposal in order to eliminate the sharp end point and thereby reduce the risk of puncture, scratching or other injury which might result from handling. Such practices are now disfavored because of the substantial danger of an accidental puncture during the breaking or cutting operations, and the recognition that the cutting tool itself can be a breeding ground for disease-causing micro-organisms.

While the used needle presents the most significant risk of injury or infection through accidental puncture or scratching of a person's skin, the used syringe may also present a risk of infection. For example, a used syringe can contain residual blood or medication which, if exposed to a person's skin, may be absorbed topically (particularly if a cut or break is present) and may cause a serious internal infection or other reaction.

As a result of the foregoing dangers, it is preferred current practice to dispose of such devices in-tact, without dismantling them. In disposing of the whole hypodermic needle and syringe, however, medical personnel would sometimes attempt to recap the used needle before disposal with the same protective cap that covered the needle during shipment from the manufacturer. This practice itself could result in accidental puncture or contact while the needle point is being recapped. Because of this danger, it is now recommended by the Center For Disease Control ("C.D.C") that needles not be recapped after use.

In order to overcome such difficulties, various retractable needle/syringe devices have been developed wherein a hypodermic needle is pre-assembled within a syringe or device housing adapted to dispense a volume of injectant, and which provides means for fixedly projecting the needle from the device to give an injection and retracting it back into the device for disposal. For example, U.S. Pat. No. 4,507,117 to Vining et al. describes a needle/syringe device wherein the needle is fixedly projected from the syringe by lockingly engaging a pair of locking members formed on the syringe plunger with a pair of recessed portions formed on the needle mounting base, and then lockingly engaging a second pair of locking members formed on the mounting base with a second pair of recessed portions formed on the neck of the syringe barrel. The plunger must be rotated clockwise to lock each pair of locking members to their respective recessed portions. To fill the syringe with medication, the plunger is unlocked from the mounting base and drawn back as in a conventional syringe. The needle is retracted after injection by unlocking the base from the neck and drawing back on the plunger.

U.S. Pat. No. 4,767,413 to Haber et al. discloses a dental syringe wherein a pre-filled ampule of medication is spring biased within a cylinder proximate a hypodermic needle. A retaining collar engaging the ampule is pushed into the cylinder to place the ampule into fluid communication with the needle and project the needle from the cylinder against the yielding spring. To keep the needle in a projected state, the operator of the device uses two fingers to compress a pair of opposed spring-like locking arms formed on the cylinder into engagement with a locking skirt formed on the retaining collar. Holding the locking arms in this position, the operator then uses his thumb to depress a plunger member into the ampule to discharge the injectant therefrom. To retract the needle, the operator releases the locking arms causing the spring to urge the ampule and needle back to their pre-injection positions.

The art also discloses retractable needle mechanisms for use in catheter insertion procedures. For example, U.S. Pat. No. 4,747,831 to Kulli discloses a needle/handle assembly wherein the needle lockingly projects outwardly from a bore formed in the handle. When the catheter has been placed, a spring activated retraction mechanism provided for the handle can be operated to automatically retract the needle into the handle.

While the foregoing devices should generally yield good results, they suffer some disadvantages. First, the Vining et al. and Haber et al. devices can be cumbersome to operate. The Vining et al. device requires multiple steps to lockingly project the needle from the syringe, requires unlocking of the plunger from the needle mounting base to draw fluid into the syringe, and requires unlocking of the base from the syringe neck to retract the needle. The Haber et al. device requires the operator to rely on finger pressure exerted by two fingers on the locking arms to hold the needle in a projected state while attempting to give the injection using a third finger of the same hand.

These injection devices suffer a further drawback where the site of the injection is critical. For example, drugs such as xylocaine and novocaine, if administered intravenously, can cause a patient to have a cardiac arhythmia which can subsequently result in death. Accordingly, these drugs must be administered intramuscularly or in fatty tissue. When a conventional needle/syringe device is used to give the injection, the syringe plunger is drawn back slightly prior to injection to "aspirate" for blood and thereby ensure that the needle has not been inadvertently placed in a patient's vein or artery. If blood appears in the injectant through the aspiration process, a new site for the injection must be chosen. Moreover, because of the potential contamination to the injectant by the blood, the injectant should be replaced. The Haber et al. device is adapted to dispense an ampule of medication and provides no means to aspirate for blood. The Vining et al. device can only aspirate for blood like a conventional syringe, and thus, cannot protect the injectant from contamination.

In the Kulli catheter insertion device discussed above, the needle is constantly in a projected state outside of the handle prior to use. As a result, there exists a greater risk of potential contamination to the needle from dropping or otherwise mishandling the device, and thus, a greater risk to persons operating the device of coming into contaminating contact with the needle.

Accordingly, it is an object of the present invention to provide new retractable needle/syringe devices which overcome the foregoing disadvantages of the prior art. It is also an object of the present invention to provide new retractable needle/syringe devices for use in blood collection, medicinal injection and catheterization procedures, which can be economically fabricated, and which are of a durable yet lightweight construction.

It is another object of the present invention to provide new retractable needle/syringe devices which are compact in size so as to be easily placed in a uniform pocket prior to use, and easily locked inside a standard hospital medication cart when unattended, thus obviating the risks caused by leaving unattended devices in a patient's room.

It is a another object of the present invention to provide new retractable needle/syringe devices wherein the entire device can be safely transported to ultimate disposal after use without need to remove the needle from the syringe, thus substantially reducing the risk of exposing the person handling the device to injury, infection, or disease by puncture or contact with the used needle or syringe.

It is yet another object of the present invention to provide new retractable needle/syringe devices for use in blood collection, medicinal injection, and catheterization procedures, wherein the needle and syringe are pre-assembled in a device housing adapted to automatically lockingly project the needle therefrom by use of a simple push button mechanism, leaving the hands of the person using the device free to operate the syringe, and safely retract the needle back into the housing after use by means of the same push button.

It is still another object of the invention to provide a retractable needle/syringe device capable of dispensing a pre-filled ampule of medicament, wherein the device can be operated to aspirate for blood prior to giving the injection, when necessary, substantially without danger of contamination to the medicament.

The foregoing specific objects and advantages of the invention are illustrative of those which can be achieved by the present invention and are not intended to be exhaustive or limiting of the possible advantages which can be realized. Thus, these and other objects and advantages of the invention will be apparent from the description herein or can be learned from practicing the invention, both as embodied herein or as modified in view of any variations which may be apparent to those skilled in the art. Accordingly, the present invention resides in the novel parts, constructions, arrangements, combinations and improvements herein shown and described.

SUMMARY OF THE INVENTION

Briefly described, the present invention comprises pre-assembled needle/syringe devices adapted for use in blood collection, catheterization, and medicinal injection procedures, each being enclosed within a device housing adapted to fixedly project the needle therefrom to perform the procedure, and, after the procedure is performed, safely retract the needle back into the housing for disposal, substantially without risk of contaminating contact by persons handling the device with a used needle or syringe.

According to one specific aspect of the invention, the retractable needle/syringe device comprises a device housing, a needle/syringe assembly, a coil spring member, and a push button locking mechanism, all integrated into a unitary assembly. The device housing is formed as a elongated, substantially tubular member having a generally flat back end portion, and a generally conical front end portion formed with an opening therethrough. The housing is further formed with an elongate window-like opening and first and second receiving apertures disposed toward the back end portion thereof.

According to the invention, the syringe provides a barrel member disposed within the housing in a first position and slidably translatable within the housing forwardly to a second position and then back again. The barrel is an elongated member having a closed back end portion and a front end portion providing a hub member adapted to fixedly engage the hub of a hypodermic needle. The barrel is formed with an elongate window-like opening which aligns with the window-like opening formed on the housing. The barrel contains a plunger member having a perpendicular operator arm connected thereto which projects out of the housing through the aligned window-like openings formed on the barrel and housing. The plunger can be backwardly and forwardly translated via the operator arm so as to draw fluid (i.e., blood from a patient's vein or the medicament to be injected from a source thereof) into the barrel and discharge it therefrom, respectively. Preferably, the barrel and at least a portion of the housing are formed from a transparent plastic material to enable the user of the device to visually observe fluid entering and exiting the syringe.

As preferably embodied, the hypodermic needle is formed with a first open end and a second open end; the first open end slidably engaging a needle hub which itself is open-ended. The needle hub is twistingly inserted into the syringe hub formed on the barrel such that the first open end of the needle projects into the syringe hub and the second open end axially aligns with the opening formed in the front end portion of the housing. The coil spring member is encirclingly retained over the needle in abutting alignment between the syringe hub and the front end portion of the housing so as to bias the barrel in the first position.

As preferably embodied, the locking mechanism comprises a push button, an extension member, a bearing portion, and a resilient arm member formed with first and second prong portions, all integrated into a unitary part. The locking mechanism is slidably received through the back end portion of the housing such that the push button projects out of the housing, and such that the bearing portion abuts the back end portion of the syringe barrel so as to maintain an abutting alignment between the locking mechanism and the syringe. The arm member is a resiliently yieldable member which projects angularly outward from the bearing portion such that the first and second prong members are received through the first and second receiving apertures, respectively, formed on the device housing.

According to the invention, when the push button is depressed into the housing, the spring will yieldingly urge the barrel member forward to the second position and the first open end of the needle will project from the housing through the opening in the front end portion thereof. At the same time, the first prong will engage the front edge of the first receiving aperture causing the resilient arm member to yieldingly urge the prong into the housing through the aperture, and, upon reaching the second receiving aperture, project the first prong thereinto. When the pressure applied to the push button is released, the resilient biasing force exerted by the spring against the barrel will bias the first prong against the back edge of the second receiving aperture so as to effectively lock the barrel in the second position and thereby fixedly maintain the needle in a projected state. With the needle fixedly projected from the housing, the device can be operated to draw blood from a patient or give an injection as desired.

After the procedure is completed, the needle can be retracted back into the housing and the device disposed of without risk to any person handling the device of contaminating contact with the used needle. To retract the needle, downward pressure is applied to the push button which will cause the second prong to engage the front edge of the second receiving aperture, thereby causing the arm member to yieldingly urge the first prong back into the housing. A subsequent release of pressure on the push button will cause the spring to resiliently expand so as to urge the barrel back to the first position, whereupon the arm member will project the first prong back into the first receiving aperture.

The entire device can then be discarded in a suitable disposal unit.

According to another specific aspect of the invention, the retractable needle/syringe device can be adapted for use as a catheter insertion device. According to this aspect of the invention, the device as hereinbefore described is provided with a catheter member slidably received over the needle. The spring is sized so as to encirclingly slide over both the cathether and the needle. The housing is sized so as to completely enclose the catheter when the needle is in a retracted state. Moreover, the opening in the front end of the housing is sized so that the catheter can be completely passed therethrough.

As preferably embodied, when the push button is depressed into the housing the needle and at least a portion of the catheter will pass through the opening formed in the front end portion of the housing and be fixedly projected therefrom. The catheter can then be inserted into the patient's vein guided by the needle. The person operating the device can thereafter check to see if the catheter has been properly placed by drawing back on the syringe plunger arm and visually observing the flow of blood into the syringe barrel. With the catheter properly placed, the push button is depressed again to retract the needle into the housing for disposal as described above.

In an alternative embodiment of the invention, most preferred for use in medicinal injection procedures, the device comprises a housing, a syringe-type barrel, a hypodermic needle, a coil spring, an ampule filled with an injectant, an ampule plunger mechanism, and a push button locking mechanism (as described above), all integrated into a unitary assembly.

According to this aspect of the invention, the housing has the same configuration as in the embodiment of the invention described above. The barrel member is disposed within the housing in a first position and is slidably translatable forwardly to a second position and back again. The barrel is formed with a generally flat back end portion, and a generally flat front end portion formed with a projecting hub member which engages the needle hub of the hypodermic needle. The barrel is further formed with an elongate window-like opening aligned with the window-like opening formed on the housing. The coil spring is encirclingly retained over the needle in abutting alignment between the barrel hub member and the front end portion of the housing so as to bias the barrel member in the first position.

According to the invention, an ampule holding an injectant is slidably frictionally received within the barrel member and is translatable forwardly and backwardly therewithin. The ampule is formed with a first seal member and a second, movable seal member disposed opposite the first seal. The ampule is provided with a plunger mechanism to facilitate forward and backward translation of the ampule. The plunger mechanism comprises a shaft member connected to the moveable second seal of the ampule, and an operator arm connected in perpendicular to the shaft and projecting out of the housing through the window-like openings formed in the barrel and housing.

According to the invention, when the push button of the locking mechanism is depressed into the housing, the spring will yieldingly urge the barrel to the second position and the needle will project from the housing through the opening in the front end portion thereof. At the same time, the locking mechanism operates to fixedly retain the barrel in that position (as described above) and thereby fixedly project the needle from the housing. The needle can then be brought into fluid communication with the injectant by applying forward pressure to the plunger operator arm to forwardly translate the ampule so as to cause the needle to penetrate the first seal. The ampule can be further forwardly translated until the first seal engages the flat front end portion of the barrel which provides a stop against further forward movement of the ampule. At that point, further forward pressure applied to the plunger arm will cause the second seal to move forward within the ampule so as to discharge the injectant from the ampule through the needle. After the injection is given, the needle can be retracted into the housing by again depressing the push button, whereafter the entire device can be safely disposed of.

Advantageously, the device provides means to "aspirate" for blood prior to administering the injection, when necessary, substantially without risk of contamination to the injectant. The frictional engagement between the barrel and the ampule enables the ampule to act similarly to a syringe plunger when the operator arm is drawn back. Accordingly, when the ampule is drawn backward via the operator arm, a negative pressure or vacuum will develop in the barrel air space ahead of the first seal. If the needle has been inadvertently inserted into a patient's vein or artery, the vacuum created in the barrel will cause blood to be drawn thereinto, which will be visually observable to the person operating the device through the transparent barrel and housing. Because the injectant is enclosed within the ampule, it is protected from interaction with and possible contamination by the blood.

It will be appreciated by those skilled in the art that the foregoing brief description and the following detailed description are exemplary and explanatory of the present invention, but are not intended to be restrictive thereof or limiting of the advantages which can be achieved by the invention. Thus, the accompanying drawings, referred to herein and constituting a part hereof, illustrate preferred embodiments of the invention and, together with the detailed description, serve to explain the principles of the invention.

BRIEF DESCRIPTION OF THE DRAWINGS

FIG. 1 is a cross-sectional view of one embodiment of the retractable needle/syringe device of the present invention showing the needle in a retracted state.

FIG. 2 is a cross-sectional view of the retractable needle/syringe device of FIG. 1 showing the needle in a fixed projected state and the syringe plunger drawn back to draw fluid into the device.

FIG. 4 is a cross-sectional view of the retractable needle/syringe device of the present invention for use in catheterization procedures showing the needle and catheter in a retracted state.

FIG. 5 is a cross-sectional view of the retractable needle/syringe device of FIG. 4 showing the needle and catheter in a fixed projected state.

DETAILED DESCRIPTION OF PREFERRED EMBODIMENTS

Figure 3A:
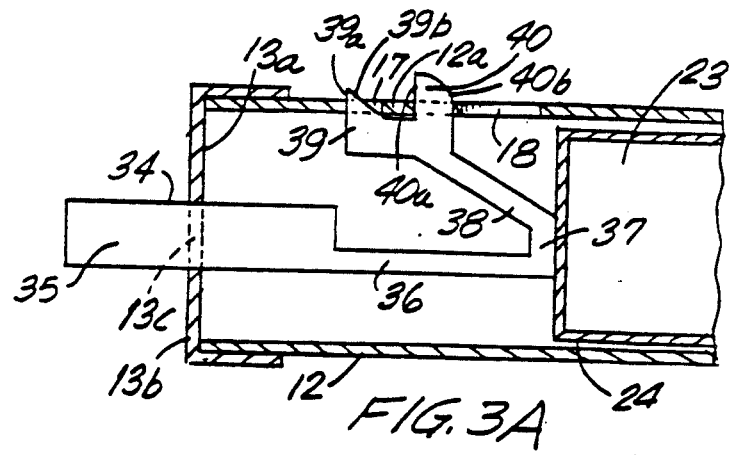
FIGS. 3A, 3B, 3C and 3D are cross-sectional views of the retractable needle/syringe device of FIGS. 1 and 2 showing the operation of the push button locking mechanism for fixedly projecting and retracting the needle.
Figure 3B:
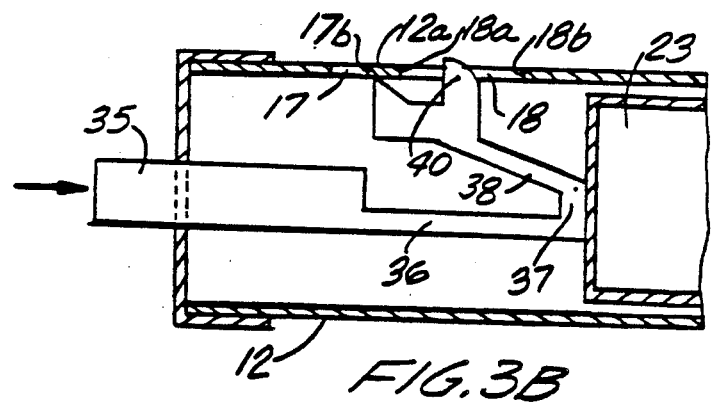
Figure 3C:
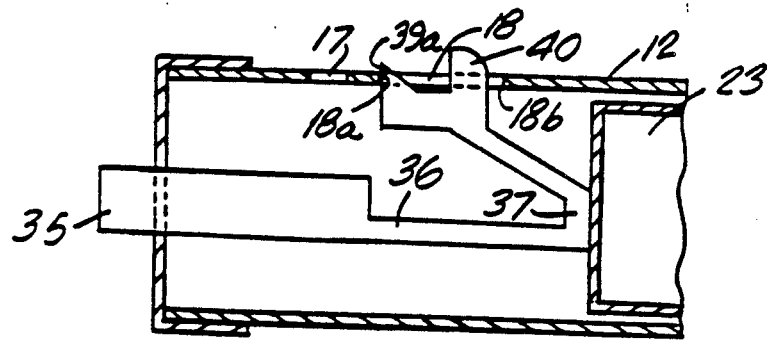
Figure 3D:
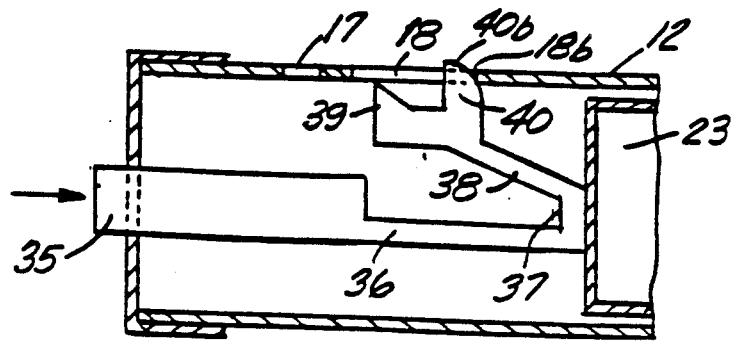

Referring now to the accompanying drawings, wherein like reference characters refer to like parts throughout the various views, there are shown in FIGS. 1-7 the preferred embodiments of the retractable needle/syringe device according to the present invention.

Referring first to FIGS. 1-3, there is shown a preferred embodiment of the present invention (indicated generally at 10) adapted for use in blood collection and medicinal injection procedures. As here embodied, retractable needle/syringe device 10 comprises a housing 12, a syringe device 21, a hypodermic needle 22, a spring member 32, and a push button locking mechanism (indicated generally at 34), all integrated into a unitary assembly as more fully described below.

According to the invention, an elongate, generally cylindrical housing 12 is provided to enclose the component parts of retractable needle/syringe device 10. As here embodied, the housing is formed with a generally flat back end portion 13 and a generally conical front end portion 15. Conical front end portion 15 is provided with an opening 15a through which needle 22 can pass so as to project from the housing. (The operation of device 10 will be fully described below). Back end portion 13 is provided with an opening 13a to receive needle/syringe assembly 20 and push button locking mechanism 34. An end cap 13b is affixed over end portion 13 to close the back end of the housing. The end cap is formed with an opening 13c to slidably receive push button 35 of locking mechanism 34. The housing is also provided with a pair of apertures 17 and 18 adjacent housing end portion 13, which are spaced apart by housing sidewall portion 12a. Apertures 17 and 18 cooperate with prongs 39 and 40 of locking mechanism 34 to facilitate the needle projection and retraction functions of the invention (described below). Moreover, housing 12 is formed with a window-like opening 16 to receive syringe plunger arm 30. Opening 16 should be proportioned to a length sufficient to allow syringe plunger arm 30 to operate within its full range of motion as described below.

As preferably embodied, housing 12 is fabricated from a moldable plastic material, at least a portion of which should be transparent so that the operator of device 10 can visually observe fluid entering and exiting the syringe. Advantageously, because of the transparent nature of the housing, the volumetric gredations which are typically displayed on the syringe barrel (not shown) are easily visible to the operator of the device. The housing should be proportioned to enclose the full length of a needle/syringe device (described below) pre-assembled for use in a blood collection or injection procedure. Preferably, the housing should be fabricated to sizes sufficient to accommodate syringes ranging from 1 to 12 millileters, and needles having a projected length from the syringe ranging from approximately 1 to 1¼ inches. It should be understood, however, that the present invention is adaptable for use with larger syringes and needles if desired.

To perform a blood collection or injection procedure, the housing is provided with a pre-assembled needle/syringe assembly (generally indicated at 20) slidably insertable therewithin. Needle/syringe assembly 20 includes a syringe 21 which fixedly engages a hypodermic needle 22. Syringe 21 includes a syringe barrel 23 having a generally flat back end portion 24, and a slightly conical front end portion 25 formed with a projecting hub member 26. Hub 26 is formed with a threaded bore 26a which extends into the interior of the syringe barrel. The barrel is preferably formed from a transparent molded plastic material similar to that of a conventional syringe.

The syringe further includes a plunger mechanism 27 frictionally slidable backward and forward within barrel 23. Plunger 27 preferably comprises a molded plastic shaft 28 integrated at the front end thereof with a rubberized, slightly conical base portion 29 adapted to seat in conical front end portion 25 of barrel 23. Base portion 29 is formed with ribs 29a which frictionally engage the interior sidewalls of the housing to form a fluid-tight seal therebetween. According to the invention, the plunger handgrip typically found in conventional syringes is eliminated and back end 24 of the syringe barrel is closed off. The handgrip is replaced by a plunger arm 30 integrated in perpendicular with shaft 28. As here embodied, plunger 27 is formed with a receiving aperture 27a into which end portion 30a of arm 30 is slidably forced so as to snappingly affix the arm to the plunger. Plunger arm 30 projects through a window-like opening 31 formed in the syringe barrel and out through window-like opening 16 formed in housing 12, which is aligned with opening 31, so as to be easily accessed by the operator of device 10. Opening 31 in syringe barrel 23 is proportioned such that plunger arm 30 can be drawn backward via finger pressure until shaft 28 abuts the interior wall of end portion 24 of the syringe barrel, and pushed forward until conical base portion 29 firmly seats in conical end portion 25.

It will be recognized by those skilled in the art that conventional needle/syringe devices are operated by gradually pulling the syringe plunger backwardly out of the syringe barrel via the handgrip so as to create an air space of increasing volume in the syringe barrel ahead of the plunger wherein fluid can be collected. The plunger is gradually pulled out of the barrel until the desired amount of fluid is drawn into the barrel up to the maximum volume of the syringe. Because the syringe barrel of the present invention is fabricated with a closed back end and a perpendicular plunger operating arm, the syringe plunger will be shorter and the barrel elongated at its back end as compared to standard syringes providing equal fluid volume so as to maintain an equivalent available fluid volume in the barrel.

In accordance with the invention, a hypodermic needle 22 is affixed to syringe 21 prior to insertion of the syringe into housing 12. As preferably embodied, needle 22 is a hollow needle member formed with a first open end 22a and a second open end 22b. Open end 22a is fixedly engaged within a needle hub 22c which itself is open-ended. The needle hub is twisted into threaded bore 26a of syringe barrel 23 so as to secure the needle to the syringe. In its retracted state, needle 22 is disposed within housing 12 so that open end 22b of the needle aligns with housing opening 15a.

As preferably embodied, the present invention provides means for fixedly projecting needle 22 out of housing 12 for use in a blood collection or injection procedure, and then safely retracting it back into the housing for disposal after the procedure has been performed. According to the invention, a coil spring member 32 surrounds needle 22 in abutting alignment between syringe hub 26 and the interior sidewall of conical end portion 15 of housing 12. Spring 32 should preferably be fabricated with a tension sufficient to keep open end 22a of needle 22 biased away from opening 15a in housing 12, yet resiliently yield in response to light forward finger pressure applied to syringe barrel 23 so as to allow needle 22 to move forward and project out of the housing.

Additionally, device 10 is provided with a push button locking mechanism 34 (see particularly FIGS. 3A–3D) slidably received through opening 13a in housing 12, which cooperates with spring 32 to facilitate the needle projection/retraction functions of the present invention (described in detail below). As here embodied, locking mechanism 34 comprises a push button 35, an extension member 36, a bearing portion 37, and a resilient arm member 38 formed with a pair of prong portions 39 and 40, all preferably fabricated from a moldable plastic material and integrated into a unitary part.

As here embodied, locking mechanism 34 is positioned within housing 12 such that bearing portion 37 abuts the exterior of syringe barrel end portion 24 so as to maintain abutting alignment between the locking mechanism and syringe 21. Arm 38 is a resiliently yieldable member which projects angularly upward within the housing from bearing portion 37 such that prongs 39 and 40 formed on arm 38 are received through housing apertures 17 and 18, respectively. According to the invention, prong 39 is formed in a generally triangular configuration, having a flat edge 39a and an integral diagonal edge 39b disposed forwardly of flat edge 39a. Prong 40 is generally formed in a quarter-circle configuration, having a flat edge 40a and an integral curved edge 40b disposed forwardly of edge 40a. Preferably, prong 40 is substantially larger than prong 39, the advantage of which will be apparent from the discussion of the operation of locking mechanism 34 below. When locking mechanism 34 is properly positioned in housing 12, push button 35 will project out of the housing through aperture 13c formed on end cap 13b. It should be apparent to those skilled in the art that push button 35 should be of a sufficient length such that, when needle 22 is fixedly projected out of the housing, a portion of the push button is still accessible to the user of device 10 for purposes of releasing the locking mechanism (as described below) and thereby retracting the needle back into the housing.

Normal operation of the fully assembled retractable needle/syringe device of the present invention (the assembly of which will be described in detail below) is initiated by depressing push button 35 into housing 12. The abutting alignment between locking mechanism 34 (via bearing portion 38), syringe barrel 23, and coil spring 32 will cause needle/syringe assembly 20 to translate forward within the housing so as to compress spring 32 and thereby allow open end 22a of needle 22 to pass through opening 15a in conical end portion 15 and project out of the housing. At the same time, diagonal edge 39b of prong 39 will engage edge 17b of aperture 17 causing arm 38 to yield inwardly, which in turn will cause prong 39 to move inwardly through aperture 17. Continued downward pressure on push button 35 will cause prong 39 to slide forward within the housing toward aperture 18 in engagement with sidewall portion 12a (see FIGS. 3A and 3B). When prong 39 reaches aperture 18, the biasing force exerted on arm 38 by the engagement of prong 39 and sidewall portion 12a will be relieved causing arm 38 to spring outward thereby causing prong 39 to be projected through aperture 18. When pressure on the push button is released, the resilient biasing force exerted by spring 32 against barrel 23 will bias flat edge 39a of prong 39 against back edge 18a of aperture 18 to prevent any backward translation of the needle/syringe assembly (see FIG. 3C). Thus, by simply depressing push button 35 into the housing and then releasing it, the needle/syringe device is automatically locked in a forward position such that open end 22b of needle 22 fixedly projects out of the housing.

With the needle fixedly projected out of housing 12, the device can be operated like a conventional syringe to draw blood from a patient or give the patient an injection. To draw blood, the needle is inserted into a patient's vein and plunger 27 is drawn back via light finger pressure applied to plunger arm 30 causing blood to be drawn into syringe barrel 23. After the desired amount of blood is drawn, the needle is removed from the patient's vein. Thereafter, light forward finger pressure can be applied to plunger arm 30 to advance plunger 27 forward and thereby discharge the blood into an appropriate collection receptacle. To give an injection of medication, the needle is inserted into a source of the injectant to be administered and plunger 27 is drawn back as described above to draw the desired amount of injectant into barrel 23. The injection can then be given in the conventional manner with the injectant being dispensed from barrel 23 by pushing plunger 27 forward via plunger arm 30.

After the appropriate procedure has been completed, the needle can be retracted back into the housing and the device disposed of. To retract the needle, downward pressure is applied to push button 35. This will cause curved edge 40a of prong 40 to engage edge 18b of aperture 18, which in turn will cause arm 38 to resiliently yield inward such that prong 39 moves into the housing through aperture 18 (see FIG. 3D). The comparatively larger dimensions of prong 40 over prong 39 allows curved edge 40a of prong 40 to maintain its engagement with edge 18a, and thereby continue to inwardly displace arm 38, until prong 39 has moved completely into the housing.

When the downward pressure on push button 35 is released, spring 32 will automatically resiliently expand so as to urge needle/syringe assembly 20 backward and retract needle 22 back into the housing through opening 15a. The abutting relationship between syringe barrel 23 and locking mechanism 34 will essentially simultaneously cause push button 35 to slide backward, with prong 39 slidably engaging sidewall portion 12a, until prong 39 reaches aperture 17. At that point, the biasing force on arm 38 caused by sidewall portion 12a will be relieved causing arm 38 to resiliently spring outward, which in turn will cause prong 39 to project into aperture 17 to return the push button to its original position. With the used needle securely retained within housing 12, the entire device can be disposed of in a suitable disposal unit, essentially without risk of contaminating contact by the person handling the device with the used needle.

According to another specific aspect of the invention, the retractable needle/syringe device can be adapted for use in catheter insertion procedures. Referring particularly to FIGS. 4 and 5, there is shown a catheter insertion device 50 which comprises retractable needle/syringe device 10 described above, and, additionally, a catheter device 51 slidably received over hypodermic needle 22. According to this aspect of the invention, spring 32 should be sized such that it can be encirclingly placed over both needle 22 and the catheter. As preferably embodied, housing 12 should be sized so that the catheter is completely enclosed therewithin when needle 22 is in a retracted state. Additionally, opening 15a in housing end portion 15 should be sized such that the catheter can be completely passed out of the housing. As preferably embodied, the present invention is particularly economically suitable for use with catheter devices ranging in length from approximately 1 to 1¼ inches. Because this aspect of the invention is more concerned with catheter placement than with blood collection, it is also preferred that 1 millileter syringes be used. It should be understood, however, that any of the syringe devices described above (i.e., 1 to 12 millileters) can be used in conjunction with the catheter device as a combination blood collection/catheter insertion apparatus.

The operation of both the needle/syringe assembly 20 and locking mechanism 34 for this aspect of the invention is identical to that described above for device 10. By depressing push button 35, end portion 22b of needle 22 and a portion of catheter 51 are automatically lockingly projected out of housing 12. The catheter is then inserted into a patient's vein guided by needle 22. The operator of the device can check to see if the catheter has been properly inserted into the vein by drawing back on syringe plunger arm 30 and visually observing the flow of blood into syringe barrel 23. With catheter 51 properly in place, the operator can then hold the catheter with one hand and depress push button 35 with the other hand to retract needle 22 back into the housing. With the used needle securely enclosed within the housing, the entire device can be safely disposed of. It will be apparent to those skilled in the art that device 50 substantially eliminates the risk inherent in conventional catheterization procedures of blood shooting out of a patient's vein and onto the skin or clothes of the person performing the procedure.

Assembly of needle/syringe device 10 and catheter insertion device 50 of the present invention are relatively straight-forward. First, needle/syringe assembly 20 is pre-assembled by twisting needle hub 22c of needle 22 into threaded bore 26a of syringe hub 26. Coil spring 32 is then encirclingly placed over needle 22. (For assembly of catheter insertion devices according to the present invention, catheter 51 is first slid over needle 22 and then spring 32 is encirclingly placed over the catheter). The assembled needle/syringe 20 and spring 32 (and catheter 51 where appropriate) are then slidably inserted into housing 12 through opening 13a until the spring abuts the interior sidewall of housing end portion 13. The syringe is positioned within the housing so as to align window-like opening 31 formed on the syringe barrel with window-like opening 16 formed on housing 12.

Next, locking mechanism 34 is slidably inserted through housing opening 13a such that bearing portion 37 is abuttingly aligned with syringe barrel 23, and such that prongs 39 and 40 are received through housing apertures 17 and 18, respectively. End cap 13b is next slipped over housing end portion 13 such that push button 35 is received through opening 13c in the end cap. The end cap can then be fixedly connected to the housing via a glue-type adherent, or by forming cooperating threads on the housing and the end cap (not shown) pursuant to which the cap can be screwed on to the housing. Finally, end portion 30a of plunger operating arm 30 can be passed through opening 16 in housing 12 and opening 31 in syringe barrel 23 and snappingly inserted into aperture 27a formed on plunger 27 to connect the operator arm to the plunger.

Figure 6:
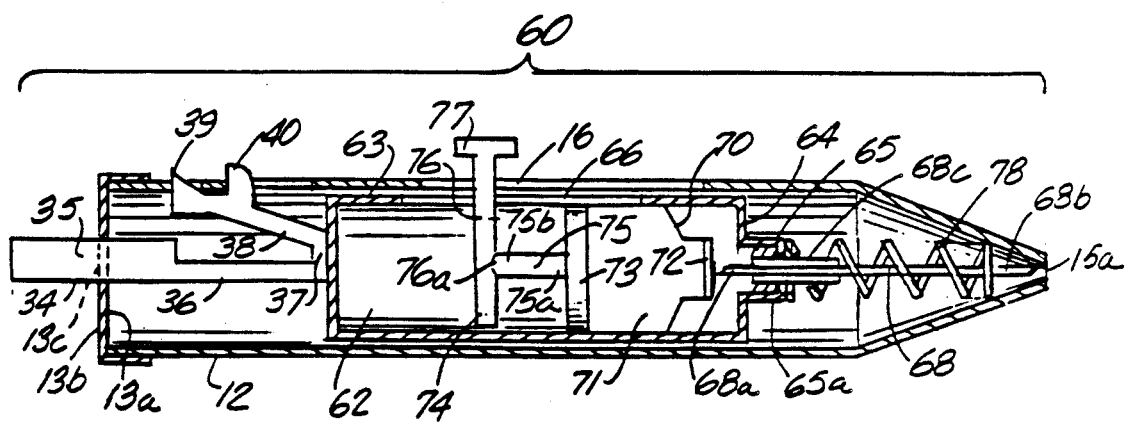
FIG. 6 is a cross-sectional view of an alternative embodiment of the retractable needle/syringe device of the present invention for use in medicinal injection procedures showing the needle in a retracted state.
Figure 7:
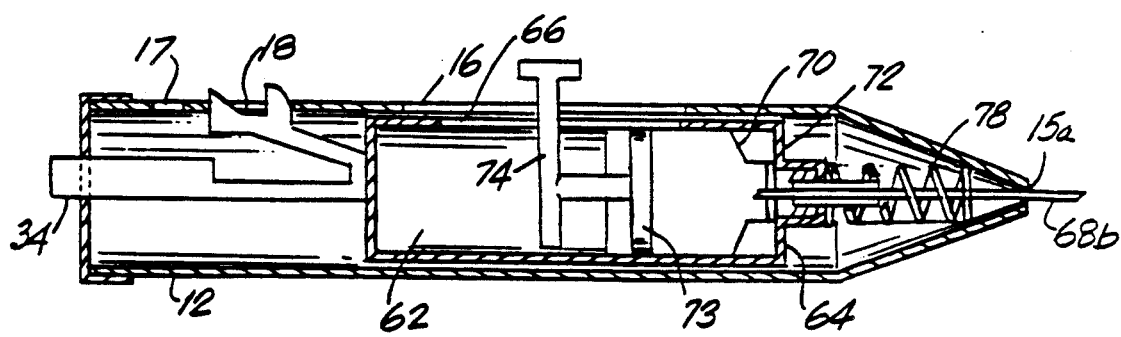
FIG. 7 is a cross-sectional view of the retractable needle/syringe device of FIG. 6 showing the needle in a fixed projected state and the injectant being discharged from the ampule.

Referring now to FIGS. 6 and 7, there is shown the most preferred embodiment of the retractable needle/syringe device of the present invention for use in medicinal injection procedures (indicated generally at reference numeral 60). Because device 60 includes some of the same elements illustrated in FIGS. 1-3 for retractable needle/syringe device 10 and hereinbefore described in detail, identical reference numerals will be used for many of these elements and a detailed description of their physical characteristics and operation will be omitted.

As preferably embodied, medicinal injection device 60 comprises a housing 12 (described above), a syringe-type barrel 62, a hypodermic needle 68, a coil spring 78, a push button locking mechanism 34 (described above), an ampule 70 filled with an injectant 71, and an ampule plunger mechanism (indicated generally at 74), all integrated into a unitary assembly as more fully described below. According to the invention, barrel 62 is formed with a closed, generally flat back end portion 63, and a generally flat front end portion 64. End portion 64 is formed with a projecting hub 65 having a threaded bore 65a extending into the barrel. Barrel 62 is further formed with an elongate window-like opening 66 aligned with opening 16 formed in housing 12. Opening 66 is dimensioned to allow sufficient forward translation of ampule 70 within barrel 62 via plunger mechanism 74 so that, as fully described below, seal 72 formed on the ampule can be punctured by needle 68 to establish fluid communication between injectant 71 and the needle.

It should be recognized by those skilled in the art that most medication ampules come in 1, 2 and 5 milliliter capacities. Accordingly, and as will be more apparent below, it is preferred that barrel 62 be fabricated to sizes adapted to slidably frictionally receive such ampules. Moreover, because plunger mechanism 74 primarily operates in a forward direction to translate the ampule into fluid communication with the hypodermic needle, and need only draw the ampule backwardly a short distance to aspirate the needle when necessary (discussed more fully below), barrel 62 can have a length significantly shorter than syringe barrel 23 used in needle/syringe device 10 described above.

As preferably embodied, hypodermic needle 68 is a hollow needle member similar to that described above for device 10, being formed with a first open end 68a and a second open end 68b. Open end 68a is fixedly engaged within a needle hub 68c which itself is open-ended. The needle hub is twisted into threaded bore 65a of barrel 62 so as to secure the needle to the barrel. Needle hub 68c is positioned on needle 68 so that a sufficient portion of the needle will extend into barrel 62 to facilitate fluid communication with injectant 71. In its retracted state, needle 68 is disposed within housing 12 so that open end 68b aligns with housing opening 15a.

According to the invention, an ampule 70 holding an injectant 71 is slidably frictionally received within barrel 62 and translatable forwardly and backwardly therewithin. Ampule 70 is preferably of a glass-type construction and is formed with a resilient first seal 72 secured to the top of the ampule, and a movable second seal 73 secured to the bottom thereof; both seals 72 and 73 being preferably fabricated from a rubber-type material.

Additionally, a plunger mechanism (indicated generally at 74) is provided to facilitate forward translation of ampule 70 so as to establish fluid communication between injectant 71 and needle 68 (discussed below). As here embodied, the plunger mechanism is fabricated from a molded plastic material similar to that of barrel 62, and includes a shaft 75 disposed longitudinally in barrel 62 and connected at one end thereof to movable seal 73. The opposite end of shaft 75 is integrated in perpendicular with a plunger arm member 76 which extends out of housing 12 through aligned longitudinal openings 66 and 16 in barrel 62 and housing 12, respectively Further, a perpendicular knob 77 is formed at the end of arm 76 exiting housing 12.

To establish fluid communication between injectant 71 and needle 68, light forward finger pressure is applied to knob 77. This will·cause ampule 70 to translate forward within barrel 62. When ampule 70 reaches open end 68a of needle 68, further forward translation of the ampule will cause open end 68a to pierce resilient seal 72 and extend into the ampule so as to contact the injectant 71. The ampule will continue its forward movement until seal 72 abuts the interior wall of front end portion 64 of barrel 62, which provides a stop against further forward movement of the ampule. In this position, further finger pressure applied to knob 77 will cause seal 73 to translate forward within ampule 70 so as to force the injectant 71 out of the ampule through needle 68.

As here embodied, retractable needle/syringe device 60 of the present invention provides the same needle projection/needle retraction advantages as retractable needle/syringe device 10 hereinbefore described. A coil spring member 78, similar to the one described above for device 10, surrounds needle 68 in abutting alignment between barrel hub 65 and the interior sidewalls of conical end portion 15 of housing 12, and serves to bias open end 68b of the needle away from opening 15a in housing 12. Push button locking mechanism 34 cooperates with spring 78 to facilitate the needle projection/retraction functions of device 60.

Normal operation of the fully assembled retractable needle/medicinal injection device of the present invention (the assembly of which will be described in detail below) is initiated by depressing push button 35 into housing 12. The abutting alignment between the locking mechanism (via bearing portion 38), barrel 62, and coil spring 78 will cause barrel 62 to translate forward within the housing so as to compress spring 78 and thereby allow open end 68b of needle 68 to pass through opening 15a in conical end portion 15 and project out of the housing. As hereinbefore described, spring 78 will bias prong 39 against edge 18b of aperture 18 so as to lock the needle in its projected state (see FIGS. 3A-3D).

With the needle fixedly projected out of housing 12, forward finger pressure can be applied to knob 77 to translate ampule 70 forward and allow open end 68a of needle 68 to puncture seal 72 and contact the injectant. Ampule 70 will continue of move forward until seal 72 abuts the interior wall of barrel end portion 64. Thereafter, the needle can be inserted under the patient's skin and continued forward finger pressure applied to knob 77 to force moveable seal 73 forward and thereby dispense injectant 71 through the needle and into the patient. After the injection has been given, push button 35 is again depressed to retract the needle back into the housing (as hereinbefore described). The entire device can then be safely disposed of in a suitable disposal receptacle.

Advantageously, device 60 of the present invention provides means to "aspirate" for blood when necessary prior to administering the injection, substantially without risk of contamination to the injectant. In accordance with the invention, ampule 70 can be translated backwardly within barrel 62 by applying backward pressure to knob 77. Because of the frictional engagement between the ampule and the barrel, backward translation of the ampule will cause a negative pressure or vacuum to develop in the barrel air space ahead of seal 72 similar to that which develops when the plunger of a syringe is drawn back. Accordingly, if needle 68 has been inadvertently inserted into a patient's vein or artery, the drawing back of knob 77 will cause blood to be drawn into barrel 62, which is easily visible to the operator of the device through the transparent housing and barrel. If this occurs, the site of the injection can be changed and the needle re-aspirated prior to the injection. Because the injectant is enclosed within the ampule, any blood entering the barrel will not come into contact with the injectant. Thus, the potential risk of contamination to the injectant through contact with a patient's blood, inherent with conventional needle/syringe devices, is effectively eliminated.

Assembly of the retractable needle/syringe device 60 of the present invention is also relatively straightforward. First, needle 68 is pre-assembled with barrel 62 by twisting needle hub 68c into threaded bore 65a of the barrel and coil spring 78 is then encirclingly placed over needle 68. End portion 75a of plunger shaft 75 is next attached to rear seal 73 of ampule 70 preferably via a glue-type adherent, or by forming an aperture on the seal (not shown) adapted to snapingly engage end 75a of the shaft. The ampule and plunger shaft are then slidably inserted into barrel 62 through window-like opening 66 such that front seal 72 formed on the ampule faces end portion 68a of needle 68. Seal 72 is maintained in a position away from the needle end portion 68a by the frictional engagement between the barrel and the ampule. The barrel, with ampule 70 and plunger shaft 75 inside, along with needle 68 and spring 78, are slidably inserted into housing 12 through opening 13a such that spring 78 abuts the interior sidewall of housing end portion 15. The barrel is then positioned so that window-like opening 66 formed on the barrel aligns with window-like opening 16 formed on the housing.

Next, locking mechanism 34 is slidably inserted into the housing through opening 13a such that bearing portion 37 abuts back end portion 63 of barrel 62, and such that prongs 39 and 40 are received through housing apertures 17 and 18, respectively. End cap 13b is then slipped over end portion 13 of the housing such that push button 35 is received through aperture 13c formed on the end cap. The end cap can then be affixed to the housing as described above for retractable needle/syringe device 10. Finally, plunger arm 76 is slidably inserted through aligned barrel and housing openings 66 and 16, respectively, and then pushed forward to snapingly insert end portion 75b of plunger shaft 75 into aperture 76a formed on the plunger arm.

It will be understood by those skilled in the art that the present invention in its broader aspects is not limited to the particular embodiments shown and described herein, and that variations may be made which are within the scope of the accompanying claims without departing from the principles of the invention and without sacrificing its chief advantages.

What is claimed is:

1. A retractable hypodermic needle/syringe device adapted for use in fluid collection and dispensing procedures, comprising:

an elongated, substantially tubular housing, said housing having a first end portion and an opposite second end portion, said second end portion having an opening therethrough;

a barrel member disposed within said housing and being formed with a front end portion adjacent said second end portion of said housing and a closed back end portion, said barrel member slidably translatable within said housing forwardly from a first position to a second position and back again;

a hollow hypodermic needle disposed adjacent said second end portion of said housing in fixed engagement with said front end portion of said barrel member, said needle formed with a first open end extending into said barrel member and a second open end axially aligned with said opening in said second end portion of said housing, said second open end of said needle passing through said opening and projecting out of said housing upon forward translation of said barrel member to said second position;

translation means for forwardly translating said barrel member within said housing from said first position to said second position;

locking means cooperating with said translation means for automatically releasably locking said barrel member in said second position and thereby maintaining said second open end of said needle in a projected state without assistance from the user of said device;

drawing and dispensing means slidably received within said barrel member, said drawing and dispensing means adapted to draw fluid into and dispense said fluid from said barrel member via said needle; and resilient means disposed within said housing to bias said barrel member in said first position, said resilient means yieldingly urging said barrel member forwardly to said second position in response to operation of said translation means so as to project said second open end of said needle from said housing, said resilient means resiliently urging said barrel member back to said first position in response to the release of said locking means such that said second open end of said needle fully retracts into said housing.

2. A retractable needle/syringe device according to claim 1, wherein said resilient means comprises a coil spring member encircling said needle in abutting alignment between said barrel member and said second end portion of said housing.

3. A retractable hypodermic needle/syringe device adapted for use in fluid collection and dispensing procedures, comprising:

an elongated, substantially tubular housing, said housing having a first end portion and an opposite second end portion, said second end portion having an opening therethrough;

a barrel member disposed within said housing and being formed with a front end portion adjacent said second end portion of said housing and a closed back end portion, said barrel member slidably translatable within said housing forwardly from a first position to a second position and back again;

a hollow hypodermic needle disposed adjacent said second end portion of said housing in fixed engagement with said front end portion of said barrel member, said needle formed with a first open end extending into said barrel member and a second open end axially aligned with said opening in said second end portion of said housing, said second open end of said needle passing through said opening and projecting out of said housing upon forward translation of said barrel member to said second position;

a piston member slidably disposed through said first end portion of said housing in abutting alignment with said back end portion of said barrel member, said piston member formed with a push button portion projecting outwardly of said housing, said piston member translating forwardly within said housing in response to forward pressure applied to said push button so as to move said barrel member from said first position to said second position;

locking means cooperating with said piston member for automatically releasably locking said barrel member in said second position and thereby fixedly projecting said second open end of said needle out of said housing, said piston member translating backwardly in response to the release of said locking means so as to allow said barrel member to return to said first position;

drawing and dispensing means slidably received within said barrel member, said drawing and dispensing means adapted to draw fluid into and dispense said fluid from said barrel member via said needle; and resilient means disposed within said housing to bias said barrel member in said first position, said resilient means yieldingly urging said barrel member forwardly to said second position in response to operation of said piston member so as to project said second open end of said needle from said housing, said resilient means resiliently urging said barrel member back to said first position in response to the release of said locking means such that said second open end of said needle fully retracts into said housing.

4. A retractable needle/syringe device according to claim 3, wherein said locking means comprises:

a resilient arm member having a first end portion integrated with said piston member and a second end portion angularly biased away from said piston member, said second end portion of said arm member formed with a first prong member and a second prong member, said housing providing first and second receiving apertures to receive said first and second prong members, respectively, when said barrel member is in said first position, said first and second receiving apertures each providing a front edge and a rear edge;

said first prong member engaging said front edge of said first receiving aperture in response to forward pressure applied to said push button causing said arm member to yieldingly urge said first prong member into said housing thence project said first prong member into said second receiving aperture, said resilient means biasing said first prong member against said rear edge of said second receiving aperture in response to subsequent release of said push button to lock said barrel member in said second position;

said second prong member engaging said front edge of said second receiving aperture in response to forward pressure applied to said push button when said barrel member is in said second position causing said arm member to yieldingly urge said first prong member back into said housing, said resilient means urging said barrel member back to said first position upon subsequent release of said push button causing said arm member to project said first prong member back into said first receiving aperture.

5. A retractable hypodermic needle/syringe device adapted for use in fluid collection and dispensing procedures, comprising:

an elongated, substantially tubular housing, said housing having a first end portion and an opposite second end portion, said second end portion having an opening therethrough;

a barrel member disposed within said housing and being formed with a front end portion adjacent said second end portion of said housing and a closed back end portion, said barrel member slidably translatable within said housing forwardly from a first position to a second position and back again;

a hollow hypodermic needle disposed adjacent said second end portion of said housing in fixed engagement with said front end portion of said barrel member, said needle formed with a first open end extending into said barrel member and a second open end axially aligned with said opening in said second end portion of said housing, said second open end of said needle passing through said opening and projecting out of said housing upon forward translation of said barrel member to said second position;

translation means for forwardly translating said barrel member within said housing from said first position to said second position;

locking means cooperating with said translation means for automatically releasably locking said barrel member in said second position and thereby fixedly projecting said second open end of said needle out of said housing;

a plunger member slidably disposed within said barrel member, said plunger member connected to an operator arm projecting out of said housing through cooperating elongated apertures formed on said barrel member and said housing, said plunger member backwardly translatable within said barrel member in response to backward pressure applied to said operator arm so as to selectively draw said fluid into said barrel member through said needle, said plunger member forwardly translatable within said barrel member in response to forward pressure applied to said operator arm so as to selectively dispense said fluid from said barrel member through said needle; and resilient means disposed within said housing to bias said barrel member in said first position, said resilient means yieldingly urging said barrel member forwardly to said second position in response to operation of said translation means so as to project said second open end of said needle from said housing, said resilient means resiliently urging said barrel member back to said first position in response to the release of said locking means such that said second open end of said needle fully retracts into said housing.

6. A retractable needle/syringe device according to claim 1, further comprising a catheter member slidably disposed over said needle, said catheter member enclosed within said housing when said barrel member is in said first position, at least a portion of said catheter member projecting out of said housing through said opening in said second end portion thereof in response to forward translation of said barrel member to said second position so as to permit the user of said device to grasp the catheter and guide it into a patient's vein via said needle.

7. A retractable hypodermic needle/syringe device adapted for use in fluid collection and dispensing procedures, comprising:
an elongated, substantially tubular housing, said housing having a first end portion and an opposite second end portion, said second end portion having an opening therethrough;
a barrel member disposed within said housing and being formed with a front end portion adjacent said second end portion of said housing and a closed back end portion, said barrel member slidably translatable within said housing forwardly from a first position to a second position and back again;
a hollow hypodermic needle member disposed adjacent said second end portion of said housing in fixed engagement with said front end portion of said barrel member, said needle formed with a first open end extending into said barrel member and a second open end axially aligned with said opening in said second end portion of said housing, said second open end of said needle passing through said opening and projecting out of said housing upon forward translation of said barrel member to said second position;
a plunger member slidably disposed with said barrel member, said plunger member being connected to an operator arm projecting out of said housing through cooperating elongated apertures formed on said barrel member and said housing, said plunger member backwardly translatable within said barrel member in response to backward pressure applied to said operator arm so as to selectively draw fluid into said barrel member through said needle, said plunger member forwardly translatable within said barrel member in response to forward pressure applied to said operator arm so as to selectively discharge said fluid from said barrel member through said needle;
translation means for forwardly translating said barrel member within said housing from said first position to said second position;
locking means cooperating with said translation means for automatically releasably locking said barrel member in said second position and thereby fixedly projecting said second open end of said needle out of said housing; and
a coil spring member encircling said needle in abutting alignment between said barrel member and said second end portion of said housing so as to bias said barrel member in said first position, said spring member yieldingly urging said barrel member forwardly to said second position in response to operation of said translation means so as to project said second open end of said needle from said housing, said spring member urging said barrel member back to said first position in response to the release of said locking means such that said second open end of said needle fully retracts into said housing.

8. A retractable needle/syringe device according to claim 7, wherein said translation means comprises a piston member slidably disposed through said first end portion of said housing in abutting alignment with said back end portion of said barrel member, said piston member formed with a push button portion projecting outwardly of said housing, said piston member translating forwardly within said housing in response to forward pressure applied to said push button so as to move said barrel member from said first position to said second position, said piston member translating backwardly in response to the release of said locking means so as to allow said barrel member to return to said first position.

9. A retractable needle/syringe device according to claim 8, wherein said locking means comprises:
a resilient arm member having a first end portion integrated with said piston member and a second end portion angularly biased away from said piston member, said second end portion of said arm member formed with a first prong member and a second prong member, said housing providing first and second receiving apertures to receive said first and second prong members, respectively, when said barrel member is in said first position, said first and second receiving apertures each providing a front edge and a rear edge;
said first prong member engaging said front edge of said first receiving aperture in response to forward pressure applied to said push button causing said arm member to yieldingly urge said first prong member into said housing thence project said first prong member into said second receiving aperture, said resilient means biasing said first prong member against said rear edge of said second receiving aperture in response to subsequent release of said push button to lock said barrel member in said second position;
said second prong member engaging said front edge of said second receiving aperture in response to forward pressure applied to said push button when said barrel member is in said second position causing said arm member to yieldingly urge said first prong member back into said housing, said resilient means urging said barrel member back to said first position upon subsequent release of said push button causing said arm member to project said first prong member back into said first receiving aperture.

10. A retractable needle/syringe device according to claim 9, further comprising a catheter member slidably disposed over said needle, said catheter member enclosed within said housing when said barrel member is in said first position, at least a portion of said catheter member projecting out of said housing through said opening in said second end portion thereof in response to forward translation of said barrel member to said second position so as to permit the user of said device to grasp the catheter and guide it into a patient's vein via said needle.

11. A retractable hypodermic needle/syringe device adapted for use in medicinal injection procedures, comprising:
an elongated, substantially tubular housing, said housing having a first end portion and an opposite end portion, said second end portion having an opening therethrough;
a barrel member disposed within said housing and being formed with a front end portion adjacent said second end portion of said housing and a closed back end portion, said barrel member slidably translatable within said housing forwardly from a first position to a second position and back again;
a hollow hypodermic needle member disposed adjacent said second end portion of said housing in fixed engagement with said front end portion of said barrel member, said needle formed with a first open and extending into said barrel member and a second open end axially aligned with said opening in said second end portion of said housing, said second open end of said needle passing through said opening and projecting out of said housing upon forward translation of said barrel member to said second position;
translation means for forwardly translating said barrel member within said housing from said first position to said second position;
locking means cooperating with said translation means for automatically releasably locking said barrel member in said second position and thereby maintaining said second open end of said needle in a projected state without assistance from the user of said device;
resilient means disposed within said housing to bias said barrel member in said first position, said resilient means yieldingly urging said barrel member forwardly to said second position in response to operation of said translation means so as to project said second open end of said needle from said housing, said resilient means resiliently urging said barrel member back to said first position in response to the release of said locking means such that said second open end of said needle fully retracts into said housing;
an ampule slidably received within said barrel member in frictional engagement therewith and containing a liquid medicament to be administered to a patient by injection, said ampule being formed with a first seal member at one end thereof, said ampule forwardly translatable within said barrel member to as to cause said first open end of said needle to penetrate said first seal member and thereby place said needle in fluid communication with said medicament, said ampule further being backwardly translatable within said barrel member so as to aspirate for blood prior to injecting said medicament;
stop means engaging said ampule so as to prevent further forward translation thereof subsequent to said needle establishing said fluid communication with said medicament; and
plunger means for forwardly translating said ampule so as to effectuate said fluid communication between said needle and said medicament and backwardly translating said ampule so as to aspirate said needle, said plunger means being adapted to selectively dispense said medicament from said ampule upon engagement of said ampule with said stop means.

12. A retractable needle/syringe device according to claim 11, wherein said resilient means comprises a coil spring member encircling said needle in abutting alignment between said barrel member and said second end portion of said housing.

13. A retractable hypodermic needle/syringe device adapted for use in medicinal injection procedures, comprising:
an elongated, substantially tubular housing, said housing having a first end portion and an opposite second end portion, said second end portion having an opening therethrough;
a barrel member disposed within said housing and being formed with a front end portion adjacent said second end portion of said housing and a closed back end portion, said barrel member slidably translatable within said housing forwardly from a first position to a second position and back again;
a hollow hypodermic needle member disposed adjacent said second end portion of said housing in fixed engagement with said front end portion of said barrel member, said needle formed with a first open end extending into said barrel member and a second open end axially aligned with said opening in said second end portion of said housing, said second open end of said needle passing through said opening and projecting out of said housing upon forward translation of said member to said second position;
a piston member slidably disposed through said first end portion of said housing in abutting alignment with said back end portion of said barrel member, said piston member formed with a push button portion projecting outwardly of said housing, said piston member translating forwardly within said housing in response to forward pressure applied to said push button so as to move said barrel member from said first position to said second position;
locking means cooperating with said piston member for automatically releasably locking said barrel member in said second position and thereby fixedly projecting said second open end of said needle out of said housing, said piston member translating backwardly in response to the release of said locking means so as to allow said barrel member to return to said first position;
resilient means disposed within said housing to bias said barrel member in said first position, said resilient means yieldingly urging said barrel member forwardly to said second position in response to operation of said piston member so as to project said second open end of said needle from said housing, said resilient means resiliently urging said barrel member back to said first position in response to the release of said locking means such that said second open end of said needle fully retracts into said housing;
an ampule slidably received within said barrel member in frictional engagement therewith and containing a liquid medicament to be administered to a patient by injection, said ampule being formed with a first seal member at one end thereof, said ampule forwardly translatable within said barrel member so as to cause said first open end of said needle to penetrate said first seal member and thereby place said needle in fluid communication with said medicament, said ampule further being backwardly translatable within said barrel member so as to aspirate for blood prior to injecting said medicament;

stop means engaging said ampule so as to prevent further forward translation thereof subsequent to said needle establishing said fluid communication with said medicament; and plunger means for forwardly translating said ampule so as to effectuate said fluid communication between said needle and said medicament and backwardly translating said ampule so as to aspirate said needle, said plunger means being adapted to selectively dispense said medicament from said ampule upon engagement of said ampule with said stop means.

14. A retractable needle/syringe device according to claim 13, wherein said locking means comprises:

a resilient arm member having a first end portion integrated with said piston member and a second end portion angularly biased away from said piston member, said second end portion of said arm member formed with a first prong member and a second prong member, said housing providing first and second receiving apertures to receive said first and second prong members, respectively, when said barrel member is in said first position, said first and second receiving apertures each providing a front edge and a rear edge;

said first prong member engaging said front edge of said first receiving aperture in response to forward pressure applied to said push button causing said arm member to yieldingly urge said first prong member into said housing thence project said first prong member into said second receiving aperture, said resilient means biasing said first prong member against said rear edge of said second receiving aperture in response to subsequent release of said push button to lock said barrel member in said second position;

said second prong member engaging said front edge of said second receiving aperture in response to forward pressure applied to said push button when said barrel member is in said second position causing said arm member to yieldingly urge said first prong member back into said housing, said resilient means urging said barrel member back to said first position upon subsequent release of said push button causing said arm member to project said first prong member back into first receiving aperture.

15. A retractable needle/syringe device according to claim 11, wherein said plunger means comprises:

a second seal member slidably received within said ampule in opposed placement to said first seal member, said second seal member movable toward said first seal member to force said medicament out of said ampule; and a plunger member slidably received within said barrel member in fixed engagement with said second seal member, said plunger member connected to an operator arm projecting out of said housing through cooperating elongated apertures formed on said barrel member and said housing, said plunger member responsive to forward pressure applied to said operator arm upon engagement of said ampule with said stop means so as to selectively move said second seal member toward said first seal member, said plunger member being further responsive to back pressure applied to said operator arm so as to draw said ampule backward within said barrel member.

16. A retractable needle/syringe device according to claim 11, wherein said stop means is provided by said front end portion of said barrel member.

17. A retractable hypodermic needle/syringe device adapted for use in medicinal injection procedures, comprising:

an elongated, substantially tubular housing, said housing having a first end portion and an opposite second end portion, said second end portion having an opening therethrough;

a barrel member disposed within said housing and being formed with a front end portion adjacent said second end portion of said housing and a closed back end portion, said barrel member slidably translatable within said housing forwardly from a first position to a second position and back again;

a hollow hypodermic needle member disposed adjacent said second end portion of said housing in fixed engagement with said front end portion of said barrel member, said needle formed with a first open end extending into said barrel member and a second open end axially aligned with said opening in said second end portion of said housing, said second open end of said needle passing through said opening and projecting out of said housing upon forward translation of said barrel member to said second position;

translation means for forwardly translating said barrel member within said housing from said first position to said second position;

locking means cooperating with said translation means for automatically releasably locking said barrel member in said second position and thereby maintaining said second open end of said needle in a projected state without assistance from the user of said device;

a coil spring member encircling said needle in abutting alignment between said barrel member and said second end portion of said housing so as to bias said barrel member in said first position, said spring member yieldingly urging said barrel member forwardly to said second position in response to operation of said translation means so as to project said second open end of said needle from said housing, said spring member urging said barrel member back to said first position in response to the release of said locking means such that second open end of said needle fully retracts into said housing;

an ampule slidably received within said barrel member in frictional engagement therewith and containing a liquid medicament to be administered to a patient by injection, said ampule formed with a first seal member at one end thereof, said ampule forwardly translatable within said barrel member so as to cause said first open end of said needle to penetrate said first seal member and thereby place said needle in fluid communication with said medicament, said ampule further being backwardly translatable within said barrel member so as to aspirate for blood prior to injecting said medicament;

stop means engaging said ampule so as to prevent further forward translation thereof subsequent to said needle establishing said fluid communication with said medicament; and plunger means for forwardly translating said ampule so as to effectuate said fluid communication between said needle and said medicament and backwardly translating said ampule so as to aspirate said needle, said plunger means being adapted to selectively dispense said medicament from said ampule upon engagement of said ampule with said stop means.

18. A retractable hypodermic needle/syringe device adapted for use in medicinal injection procedures, comprising:
    an elongated, substantially tubular housing, said housing having a first end portion and an opposite second end portion, said second end portion having an opening therethrough;
    a barrel member slidably received within said housing and being formed with a front end portion adjacent said second end portion of said housing and a closed back end portion, said barrel member slidably translatable within said housing forwardly from a first position to a second position and back again;
    a hollow hypodermic needle member disposed adjacent said second end portion of said housing in fixed engagement with said front end portion of said barrel member, said needle formed with a first open end extending into said barrel member and a second open end axially aligned with said opening in said second end portion of said housing, said second open end of said needle passing through said opening and projecting out of said housing upon forward translation of said barrel member to said second position;
    a piston member slidably disposed through said first end portion of said housing in abutting alignment with said back end portion of said barrel member, said piston member formed with a push button portion projecting outwardly of said housing, said piston member translating forwardly within said housing in response to forward pressure applied to said push button so as to move said barrel member from said first position to said second position;
    locking means cooperating with said piston member for automatically releasably locking said barrel member in said second position and thereby fixedly projecting said second open end of said needle out of said housing, said piston member translating backwardly in response to the release of said locking means so as to allow said barrel member to return to said first position;
    a coil spring member encircling said needle in abutting alignment between said barrel member and said second end portion of said housing so as to bias said barrel member in said first position, said spring member yieldingly urging said barrel member forwardly to said second position in response to operation of said piston member so as to project said second open end of said needle from said housing, said spring member urging said barrel member back to said first position in response to the release of said locking means such that second open end of said needle fully retracts into said housing;
    an ampule slidably received within said barrel member in frictional engagement therewith and containing a liquid medicament to be administered to a patient by injection, said ampule formed with a first seal member at one end thereof, said ampule forwardly translatable within said barrel member so as to cause said first open end of said needle to penetrate said first seal member and thereby place said needle in fluid communication with said medicament, said ampule further being backwardly translatable within said barrel member so as to aspirate for blood prior to injecting said medicament;
    stop means engaging said ampule so as to prevent further forward translation thereof subsequent to said needle establishing said fluid communication with said medicament; and
    plunger means for forwardly translating said ampule so as to effectuate said fluid communication between said needle and said medicament and backwardly translating said ampule so as to aspirate said needle, said plunger means being adapted to selectively dispense said medicament from said ampule upon engagement of said ampule with said stop means.

19. A retractable needle/syringe device according to claim 18, wherein said locking means comprises:
    a resilient arm member having a first end portion integrated with said piston member and a second end portion angularly biased away from said piston member, said second end portion of said arm member formed with a first prong member and a second prong member, said housing providing first and second receiving apertures to receive said first and second prong members, respectively, when said barrel member is in said first position, said first and second receiving apertures each providing a front edge and a rear edge;
    said first prong member engaging said front edge of said first receiving aperture in response to forward pressure applied to said push button causing said arm member to yieldingly urge said first prong member into said housing thence project said first prong member into said second receiving aperture, said resilient means biasing said first prong member against said rear edge of said second receiving aperture in response to subsequent release of said push button to lock said barrel member in said second position;
    said second prong member engaging said front edge of said second receiving aperture in response to forward pressure applied to said push button when said barrel member is in said second position causing said arm member to yieldingly urge said first prong member back into said housing, said resilient means urging said barrel member back to said first position upon subsequent release of said push button causing said arm member to project said first prong member back into said first receiving aperture.

20. A retractable needle/syringe device according to claim 11, wherein said plunger means comprises:
    a second seal member slidably received within said ampule in opposed placement to said first seal member, said second seal member movable toward said first seal member to force said medicament out of said ampule; and
    a plunger member slidably received within said barrel member in fixed engagement with said second seal member, said plunger member connected to an operator arm projecting out of said housing through cooperating elongated apertures formed on said barrel member and said housing, said plunger member responsive to forward pressure applied to said operator arm upon engagement of said ampule with said stop means so as to selectively move said second seal member toward said first seal member, said plunger member being further responsive to back pressure applied to said operator arm so as to draw said ampule backward within said barrel member.

21. A retractable needle/syringe device according to claim 15, wherein said stop means is provided by said front end portion of said barrel member.

* * * * *